United States Patent [19]

Ichimura et al.

[11] Patent Number: 4,916,406
[45] Date of Patent: Apr. 10, 1990

[54] AUTOMATIC GAIN CONTROL CIRCUIT

[75] Inventors: Kiyoshi Ichimura, Tokyo; Kozo Yasuhara, Nishinomiya; Norio Kawashima, Tokyo, all of Japan

[73] Assignee: Mitsubishi Rayon Co., Ltd., Tokyo, Japan

[21] Appl. No.: 316,062

[22] Filed: Feb. 27, 1989

[30] Foreign Application Priority Data

Feb. 25, 1988 [JP] Japan ................................ 63-43165
Feb. 25, 1988 [JP] Japan ................................ 63-43166

[51] Int. Cl.⁴ .......................... H03G 3/10; H03F 3/08
[52] U.S. Cl. ..................................... 330/281; 330/308
[58] Field of Search ............... 330/51, 59, 124, 137, 330/278, 279, 281, 308; 356/432, 433, 445, 448

[56] References Cited

U.S. PATENT DOCUMENTS 3,652,944  3/1972  Querry ............................ 330/281 X
4,040,747  8/1977  Webster .......................... 356/448 X

OTHER PUBLICATIONS

Practical Electronic Circuit Handbook (published by CQ Publishing Co. Ltd., 1978) (Title page and pp. 375-376, no English language translation provided).

Primary Examiner—Steven Mottola
Attorney, Agent, or Firm—Lowe, Price, LeBlanc, Becker & Shur

[57] ABSTRACT

An automatic gain control circuit comprising an input terminal means for receiving first and second signals, an amplifier for receiving and amplifying first and second signals and outputting a first output signal when receives the first signal and outputting a second output signal when receives the second signals, input means for receiving an operation control signal and responsive to the operation control signal for separately inputting the first and second signals to the amplifier with a predetermined interval of time, control signal generating means responsive to the second output signal of the amplifier for generating a control signal, selection means connected to the input means for supplying the second output signal of the amplifier to the control signal generating means when the second signal is fed to the amplifier and sending out the first output signals to an external circuit when the first signal is fed to the amplifier and gain control means connected to the amplifier and the control signal generating means and responsive to the control signal for regulating the gain of the amplifier, wherein the control signal generating means includes gain maintaining means for maintaining the regulated gain of the amplifier.

6 Claims, 5 Drawing Sheets

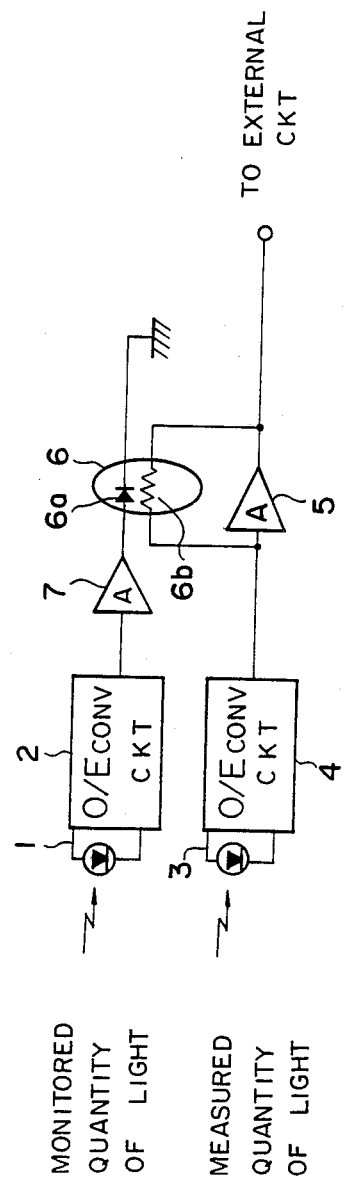

AUTOMATIC GAIN CONTROL CIRCUIT

BACKGROUND OF THE INVENTION

1. Field of the Invention

This invention relates to an automatic gain control circuit (hereunder referred to simply as an AGC circuit) and more particularly to an AGC circuit adapted for an apparatus for measuring a physical quantity relating to energy of light or the like such as a reflectivity (or reflectance) and transmissivity (or transmittance) of an object.

2. Description of the Related Art

FIG. 5 shows an AGC circuit of related art adapted for, specially, a sensing circuit for measuring a reflectivity and transmissivity of an object. In the circuit of this figure, when a light receiving element 1 generates a signal corresponding to a monitored quantity of light, an optical-to-electric (O/E) conversion circuit 2 converts the generated signal into a monitoring signal representing the monitored quantity of light. On the other hand, when a light receiving element 3 produces a signal indicating the measured quantity of light, an optical-to-electric conversion circuit 4 converts this signal into another signal of which magnitude is proportional to the measured or observed quantity of light. The output signal of the optical-to-electric conversion circuit 4 is inputted into an amplifier 5, an output of which is in turn used to calculate the reflectivity and transmissivity of the object. The amplifier 5 is provided with a CdS cell 6 as means for regulating a gain of the AGC circuit. In this case, the CdS cell 6 comprises a heating element 6a and a temperature detecting resistor 6b. This resistor 6b is connected between input and output terminal of the optical-to-electric conversion circuit 2. Further, an output of the optical-to-electric conversion circuit 2 is inputted into an amplifier 7, the amplified output of which is arranged to be applied to the heating element 6a of the CdS cell 6.

In the arrangement shown in this figure, if, for example, the monitored quantity of light is constant, the gain of the amplifier 5 remains constant and further a signal, of which magnitude is proportional to the measured quantity of light, is obtained by the amplifier 5. In a case where the observed quantity of light reflected by or transmitted through an object is reduced from the previously observed quantity of light reflected by or transmitted through another object of the same reflectivity or transmissivity due to change in quantity of light emitted from a source (not shown), an output of the optical-to-electric conversion circuit 4, as well as an output of the optical-to-electric conversion circuit 2, is also reduced. Further, the reduction of the output of the optical-to-electric conversion circuit 2 causes reduction of an output of the amplifier 7 as well as reduction of electric current flowing through the heating element 6a of the CdS cell 6, resulting in increase of the resistance of the temperature detecting resistor 6b. Thereby, the gain of the amplifier 5 increases to make up an amount of the reduction in the output of the optical-to-electric conversion circuit 4.

Thus, even if quantity of light radiated from the source of light varies, the change in the observed quantity of light can be automatically compensated.

As above described, the AGC circuit of the related art comprises the amplifier 5 having the CdS cell 6 to which a signal (hereunder sometimes referred to simply as a measuring signal) representing the observed quantity of light and further comprises another amplifier 7. A signal (hereunder sometimes referred to simply as a monitoring signal) representing the monitored quantity of light is applied to the amplifier 7 and thereafter an output of the amplifier 7 is applied to the CdS cell 6, whereby the above described AGC circuit of the related art can control the gain of the amplifier 5 to prevent the change in magnitude of the monitoring signal from effecting an output of the amplifier 5. Thus, the AGC circuit of the related art has been widely used in not only measurement of a reflectivity and transmissivity of an object but also evaluation of a ratio of quantity of a certain kind of energy issued from a source to quantity of another kind of energy converted therefrom. In the case of the above described AGC circuit of the related art, it is necessary but very difficult to equalize the amplifiers 5 and 7 with each other in all characteristics thereof to improve the precision of measurement. Practically, it is impossible to equalize the amplifiers in temperature coefficient and drift. Thus, the AGC circuit of the related art has encountered a problem that the precision of measurement is limited below a certain undesirable value due to the variation in characteristics of the amplifiers.

The present invention is accomplished to resolve the above described problem of the related art.

It is therefore an object of the present invention to provide an AGC circuit which can significantly improve the precision of measurement.

SUMMARY OF THE INVENTION

In accordance with the present invention, there is provided an AGC circuit wherein a first signal representing a physical quantity to be measured and a second signal used to control the gain of an amplifier for amplifying the first signal are separately inputted with a predetermined interval of time into the amplifier, the gain of which is controlled or regulated by using a signal outputted from the amplifier at the time of inputting the second signal thereinto, and the first signal is amplified by the amplifier and further the amplified signal is outputted therefrom, with the regulated gain remaining constant.

Namely, in accordance with the present invention, there is provided an AGC circuit comprising an input terminal means for receiving a first and second signals, an amplifier for receiving and amplifying a first and second signals and outputting a first output signal when receives the first signal and outputting a second output signal when receives the second signals, input means for receiving an operation control signal and responsive to the operation control signal for separately inputting the first and second signals to the amplifier with a predetermined interval of time, control signal generating means responsive to a second output signal of the amplifier for generating a control signal, selection means connected to the input means for supplying the second output signal of the amplifier to the control signal generating means when the second signal is fed to the amplifier and sending out the first output signals to an external circuit when the first signal is fed to the amplifier and gain control means connected to the amplifier and the control signal generating means and responsive to the control signal for regulating the gain of the amplifier, wherein the control signal generating means includes gain maintaining means for maintaining the regulated gain of the amplifier. Thereby, the physical quantity such as a reflectivity being measured by the apparatus provided with the AGC circuit of the present invention can be substantially free from effects of change in temperature characteristics and drift characteristics of the amplifier of the AGC circuit. Thus, the apparatus provided with the AGC circuit of the present invention can effect measurement of a physical quantity more precisely than the related art does.

BRIEF DESCRIPTION OF THE DRAWINGS

Other features, objects and advantages of the present invention will become apparent from the following description of preferred embodiments with reference to the drawings in which like reference characters designate like or corresponding parts throughout several views, and in which:

FIG. 5 is a circuit diagram for showing the AGC circuit of the related art.

DETAILED DESCRIPTION OF PREFERRED EMBODIMENTS

Figure 1:
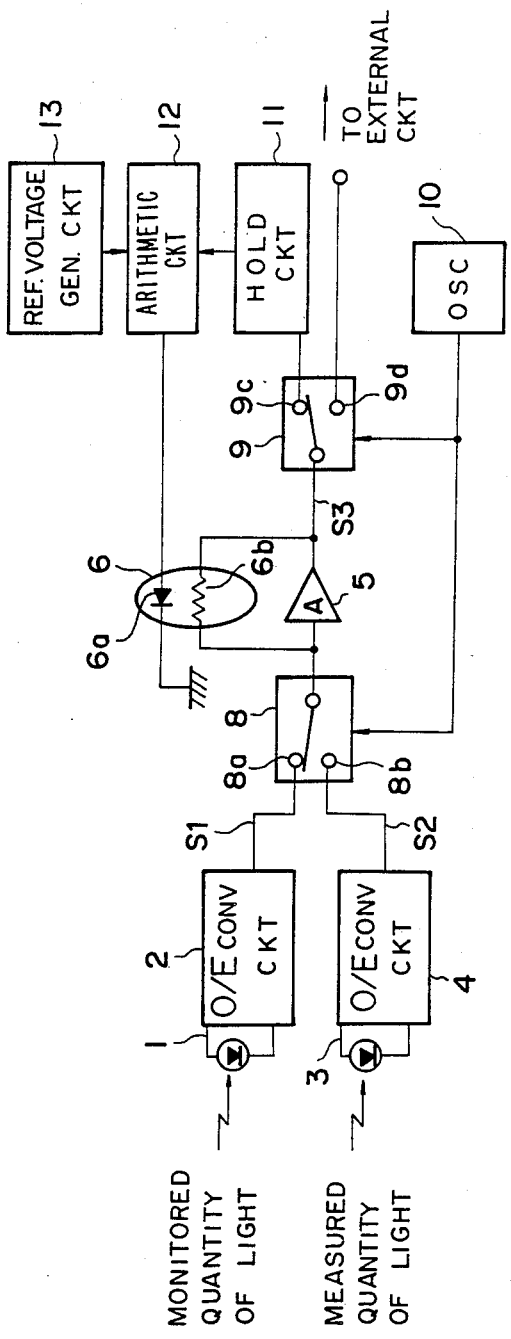
FIG. 1 is a circuit diagram for showing an AGC circuit embodying the present invention.

Hereinafter, a preferred embodiment of the present invention will be described with reference to the accompanying drawings. FIG. 1 shows the AGC circuit pursuant to the present invention which is applied to a sensing circuit for measuring a reflectivity and transmissivity of an object. In this figure, like reference characters indicate like elements shown in FIG. 5. The AGC circuit shown in this figure is provided with switching circuits 8 and 9, an oscillating circuit 10, a hold circuit 11, an arithmetic circuit in the form of a comparator 12 and a reference voltage generating circuit 13 in place of the amplifier 7 shown in FIG. 5.

The switching circuit 8 is connected to an input portion of the amplifier 5. When an actuator of the switch 8 is connected to a fixed contact 8a, an output signal S1 of the optical-to-electric conversion circuit 2 is inputted to the amplifier 5. On the other hand, when the actuator is connected to the contact 8b, an output signal S2 of the optical-to-electric conversion circuit 4 is inputted to the amplifier 5. The switching circuit 9 is connected to an output portion of the amplifier 5. When an actuator is connected to a contact 9c, an output signal S3 of the amplifier 5 is supplied to the hold circuit 11. Further, when connected to a contact 9d, the output signal S3 is further sent to an external circuit (not shown) whereupon the output signal S3 is used for calculation of the reflectivity and transmissivity. Moreover, the oscillating circuit 10 is provided in the AGC circuit which is responsive to an operation control signal inputted from a keyboard (not shown) to generate a signal (hereunder referred to simply as a timing signal) which is used to control timing of simultaneously changing the connections in the switching circuits 8 and 9. When the actuator of the switching circuit 8 is connected to the contact 8a, the actuator of the switching circuit 9 is connected to the contact 9c. Further, when the actuator of the switching circuit 8 is connected to the contact 8b, the actuator of the switching circuit 9 is connected to the contact 9d.

Thus, the switching circuit 8 operates as means for separately inputting at a predetermined interval of time into the amplifier 5 an output signal S2 (hereunder sometimes referred to as a first signal) representing an observed value of a physical quantity to be measured and an output signal S1 (hereunder sometimes referred as a second signal) used for producing a control signal which will be described hereinbelow. Further, the switching circuit 9 operates as means for feeding the output signal of the amplifier 5 to means (which will be also described hereinbelow) for producing the control signal when the second signal is supplied to the amplifier 5 and also functions as selection means for sending the output signal of the amplifier 5 to the external circuit when the first signal is supplied to the amplifier 5.

Moreover, in a case where an input voltage is applied to the hold circuit 11 at an instant t1 of time as shown in FIG. 2(a), the hold circuit 11 is adapted to output a signal a very short time later after the time t1, at which the input voltage is removed therefrom, and further adapted to continue outputting the signal thereafter in such a manner that the magnitude of the signal is maintained at the value thereof immediately before the time t1, as shown in FIG. 2(b).

Furthermore, the comparing circuit 12 is with two inputs, one of which is an output of the hold circuit 11 and the other of which is an output of the reference voltage generating circuit 13, and is further adapted to issue an output signal to the heating element 6a of the CdS cell 6 so that the inputs are substantially equal in magnitude with each other.

Additionally, the hold circuit 11, the arithmetic circuit 12 and the reference voltage circuit 13 operate as means for producing control signals to be used for controlling the gain of the amplifier 5.

Hereafter, an operation of this embodiment of the present invention as constructed as above described will be explained.

First, there is outputted from the optical-to-electric conversion circuit 2 the signal S1 of which the magnitude is proportional to the monitored quantity of light. On the other hand, there is outputted from the optical-to-electric conversion circuit 4 the signal S2 of which there magnitude is also proportional to the monitored quantity of light.

Further, the oscillating circuit 10 synchronously causes the switching circuit 8 and 9 to change the connections therein. When the actuator of the switching circuit 8 is connected to the contact 8a and further the actuator of the switching circuit 9 is connected to the contact 9c, the signal S1 is amplified by the amplifier 5. Furthermore, the amplified signal S3 is outputted from the amplifier 5 and then received by the hold circuit 11.

Figure 2:
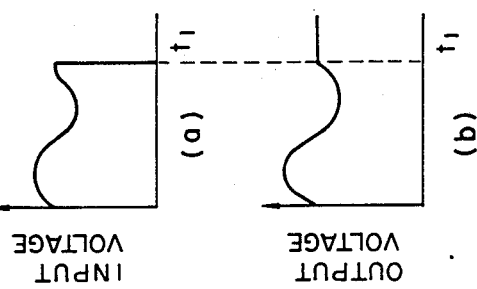
FIG. 2 is a timing chart for illustrating an operation of the embodiment of FIG. 1.

Subsequently, the hold circuit 11 outputs to the arithmetic circuit 12 the voltage corresponding to the input voltage as shown in FIGS. 2 (a) and (b). Further, the arithmetic circuit 12 applies such a voltage to the heating element of the CdS cell 6 that the output voltage of the hold circuit 11 is equal to that of the reference voltage generating circuit 13.

As a result of this, the gain of the amplifier 5 increases when the output signal S1 of the optical-to-electric conversion circuit 2 is small in magnitude while the gain of the amplifier 5 decreases when the signal S1 from the optical-to-electric conversion circuit 2 increases in magnitude.

Next, if the oscillating circuit 10 causes the actuator of the switching circuit 8 to be connected to the contact 8b at the time t1 and simultaneously causes the actuator of the switching circuit 9 to be connected to the contact 9d, the input and output voltages immediately before the time t1 are maintained by the hold circuit 11 after the time t1 as shown in FIGS. 2 (a) and (b). Further, the gain of the amplifier 5 is also maintained at the value immediately before the time t1.

Further, in this state of the AGC circuit, the output signal S2 of the optical-to-electric conversion circuit 4 is applied to the amplifier 5. Moreover, the output signal S3 of the amplifier 5 is used for calculation of the reflectivity and transmissivity.

Thus, the gain of the amplifier 5 increases (or decreases) in response to increase (or decrease) in magnitude of the signal S2 outputted from the optical-to-electric conversion circuit 4 due to variation in the quantity of light emitted from the source of light. Thus, even when the quantity of light emitted from the sources changes, the AGC circuit of the present invention can compensate for variation in the observed value of the physical quantity to be measured.

In this case, the gain controllable amplifier compensates for change in the observed value due to variation in characteristics of the amplifier itself. Thereby, it can prevent occurrence of an error in an observed value resulting from differences in characteristics between the amplifiers and further significantly improve the precision of measurement.

Figure 3:
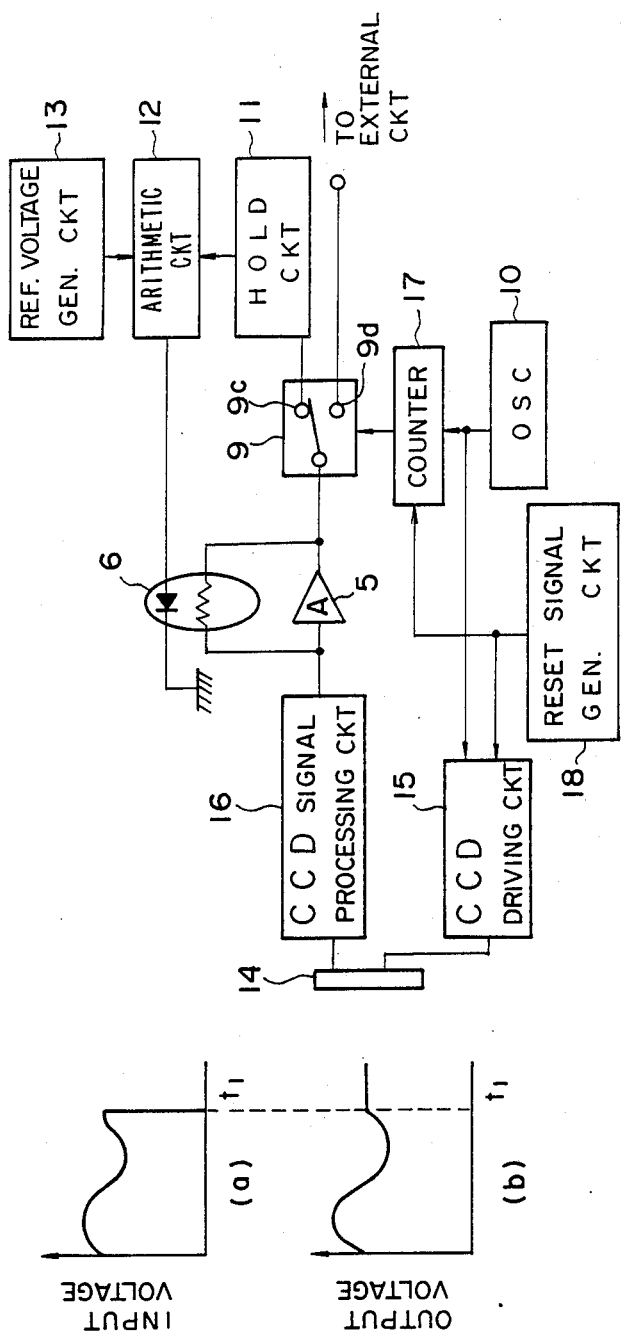
FIG. 3 is a circuit diagram for showing another embodiment of the present invention.

Turning now to FIG. 3, there is shown another preferred embodiment of the present invention. In this figure, like reference characters indicate like elements shown in FIG. 1. Further, this embodiment is provided with a charge coupled device (CCD) 14, a CCD driving circuit 15 for driving the CCD 14 and a CCD-signal-processing circuit 16 for processing an output signal of the CCD driving circuit and supplying a voltage signal to the amplifier 5, instead of the light receiving elements 1 and 3 and the optical-to-electric conversion circuit 2 and 4 as provided in the embodiment shown in FIG. 1. In addition to such elements, the embodiment of FIG. 3 is further provided with a counter 17 for counting output pulses of the oscillator 10 and a reset signal generating circuit 18 responsive to an operation control signal inputted from the keyboard (not shown) for use in resetting the counter 17 and the CCD driving circuit 15, in place of the switching circuit 8 as shown in FIG. 1.

In the AGC circuit of FIG. 3, the CCD driving circuit 15 drives the CCD 14 by using the output pulses of the oscillator 10 and further the counter 17 counts the pulses. When the CCD driving circuit 15 drives the CCD 14, the monitored quantity of light from the source of light is represented by a specific bit, for example, a first bit indicated by the CCD 14, a second signal representing the monitored quantity of light is outputted therefrom. Further, the observed or measured quantity of light from an object to be measured is represented by another bit indicated by the CCD 14 and a first signal representing the measured quantity of light is outputted therefrom. The CCD-signal-processing circuit 16 sequentially outputs these signals representing data of the quantity of light as data varying with time which are to be treated in time series. That is, the circuit 16 outputs the first and second signals by turns to the amplifier 5. Thus, although a switching circuit corresponding to the circuit 8 of the embodiment shown in FIG. 1 is not provided in this AGC circuit, the first and second signals are separately supplied to the amplifier 5 at a certain interval of time. In this process, the counter 17 causes the switching circuit 9 to change the connection therein in accordance with the counted value. That is, the actuator of the switching circuit 9 is connected to the contact 9c at the time of applying the signal representing data indicated by the first bit to the amplifier 5 and is alternatively connected to the contact 9d at the time of applying the signal representing data indicated by the second bit or another one of the remaining bits to the amplifier 5.

Further, the gain of the amplifier 5 is controlled in response to the monitored quantity of light represented by the second signal in the manner as above described in the explanation of the embodiment of FIG. 1. The voltage signal corresponding to the observed quantity of light represented by the first signal outputted from the amplifier 5 of such a gain is provided to the external circuit to calculate the reflectivity and transmissivity of an object.

Furthermore, the reset signal generating circuit 18 resets the CCD driving circuit 15 such that the driving circuit 15 scans the CCD 14 repeatedly, and simultaneously resets the counter 17. Thus, the change in the measured or observed quantity of light due to the variation in quantity of light from the source is compensated every period of time of driving the CCD 14.

Accordingly, this embodiment also compensates the change of the measured quantity of light due to the variation in characteristics of the amplifier by using the amplifier itself, thereby significantly improving the precision of measurement as the former embodiment does.

These two embodiments control or regulate the gain of the amplifier 5 by maintaining the output of the amplifier 5 by use of the hold circuit 11. Further, the amplifier 5 is adapted to amplify the first signal S2 representing the observed quantity of light corresponding to the physical quantity to be measured in such a manner that the regulated gain of the amplifier remains. Namely, the hold circuit 11 is used as means for maintaining the regulated gain of the amplifier. In a case where the amplifier 5 consists of digital circuits, an appropriate memory may be employed in place of the hold circuit 11. Further, the comparing circuit 12 can be used as means for maintaining the regulated gain of the amplifier because the magnitude of the control signal can remain constant by maintaining that of the output signal thereof.

In each of the forgoing embodiments, the AGC circuit of the present invention is applied to a circuit for measuring the reflectivity and transmissivity of an object. It is our intention that the present invention be not limited by any of the details of description and can be applied to most of the apparatus for using a kind of a source of energy and measuring a ratio of quantity of energy emitted from the source of quantity of another kind of energy converted therefrom.

Figure 4A:
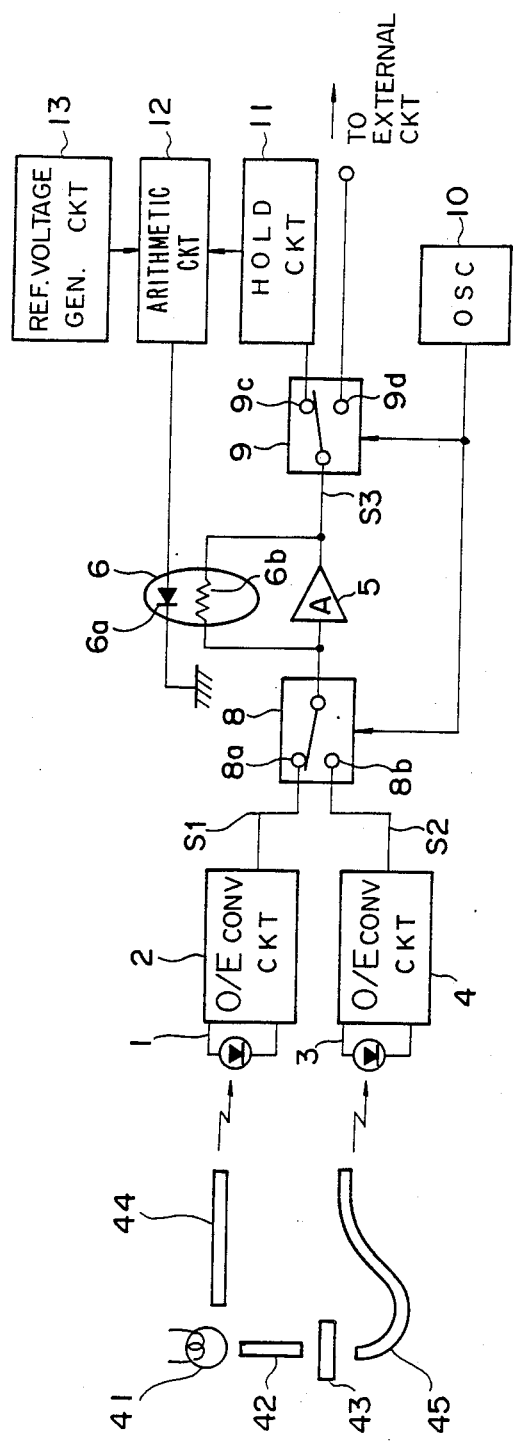
FIG. 4 (a) and (b) are circuit diagrams each showing a sensing circuit employing the AGC circuit according to the present invention.
Figure 4B:
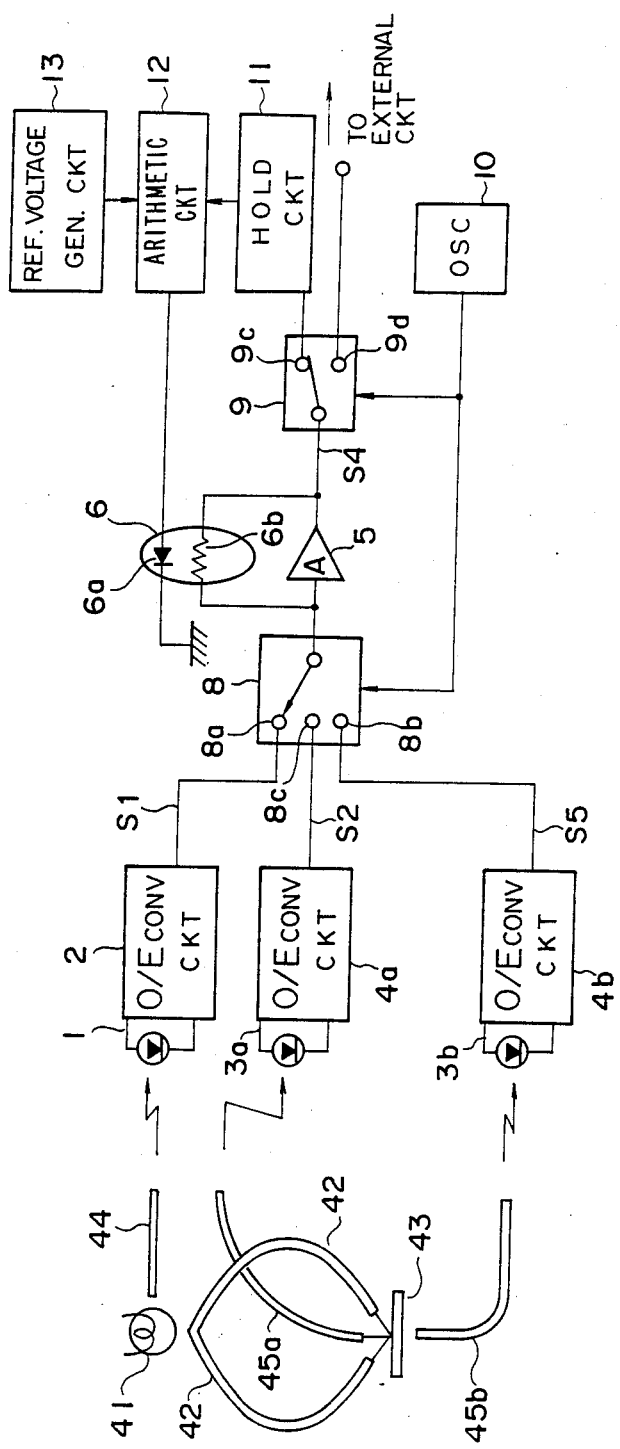

FIGS. 4 (a) and (b) are schematic block diagrams for showing an example of application of the AGC circuit of the present invention, in which like reference characters indicate like elements shown in FIG. 1. FIG. 4 (a) shows a sensing circuit for measuring a transmissivity of an object 43 and FIG. 4 (b) shows another sensing circuit for measuring a reflectivity and transmissivity of the object 43. Further, the sensing circuit shown in FIG. 4 (a) is provided with a light irradiating portion for irradiating the object 43 by transmitting light radiated from a source 41 of light through an optical fiber 42 to the surface of the object 43, in addition to the elements shown in FIG. 1. In this sensing circuit, another optical fiber 44 is provided for transmitting part of the light from the source 41 to the light receiving element 1 shown in FIG. 1 and still another optical fiber 45 is further provided for transferring light transmitted through the object 43 to the light receiving element 3, whereby a sensing portion of this sensing circuit can be small in size and thus this sensing circuit can be used for measurement of physical quantities of various objects.

Turning now to FIG. 4 (b), there is shown another sensing circuit as another example of application of the AGC circuit of the present invention. As can be easily seen from FIG. 4 (b), this sensing circuit is different in construction from the sensing circuit of FIG. 4 (a) in that an optical fiber 45a, a light receiving element 3a and an optical-to-electric (O/E) conversion circuit 4a are further provided therein in such a manner to be able to measure a reflectivity of the object 43. Thus, a switching circuit 8a is not equivalent to the switching circuit 8 and is adapted to receive output signals S1, S2 and S5 of optical-to-electric conversion circuits 2, 4a and 4b. Further, the oscillating circuit 10 generates a timing signal for making the switching circuits 8 and 9 to simultaneously change the connections therein. When the actuator of the switching circuit 8 is connected to the contact 8a, the actuator of the switching circuit 9 is connected to the contact 9c. Further, when the actuator of the switching circuit 8 is connected to the contact 8b or 8c, the actuator of the switching circuit 9 is connected to the contact 9d.

Thereby, the sensing circuit of FIG. 4 (b) can be small and used for measurement of the reflectivity and transmissivity of various objects.

While the preferred embodiments of the present invention have been described, it is to be understood modifications will be apparent to those skilled in the art without departing from the spirit of the invention. The scope of the present invention, therefore, is to be determined solely by the appended claims.

What is claimed is:

1. An automatic gain control circuit comprising:
   input means (1, 2, 3, 4; 14, 15) for receiving first and second input signals and providing first (S2) and second (S1) signals;
   an amplifier (5) for receiving and amplifying said first and second signals and outputting a first output signal in receipt of said first signal and outputting a second output signal in receipt of said second signal;
   input control means (8, 10; 10, 16, 17, 18) responsive to an operation control signal for separately supplying said first and second signals to said amplifier with a predetermined time interval therebetween;
   control signal generating means (11, 12, 13) responsive to said second output signal of said amplifier for generating a control signal, said control signal generating means including a hold circuit for holding said second output signal of said amplifier, and an arithmetic circuit connected for receiving as two input signals thereof an output signal from said hold circuit and a reference signal, said arithmetic circuit responsive to said two input signals for generating said control signal as a function of a difference between said two input signals;
   selection means (9) connected to said input control means for supplying said second output signal of said amplifier to said control signal generating means when said second signal is fed to said amplifier and sending out said first output signal to an external circuit when said first signal is fed to said amplifier; and
   gain control means (6) connected to said amplifier and to said control signal generating means and responsive to said control signal for regulating the gain of said amplifier such that said gain increases and decreases in accordance with said control signal.

2. An automatic gain control circuit as set forth in claim 1, wherein said input control means includes means (10) for generating a predetermined timing signal and means (8) for outputting one of the first and second signals selected in accordance with the timing signal, and wherein said selection means (9) is responsive to the timing signal for exchanging the operations of supplying the first output signal to the external circuit and the second output signal to said control signal generating means.

3. An automatic gain control circuit as set forth in claim 1, wherein said input control means includes means (10) for generating a predetermined timing signal and means (8) for alternately outputting the first and second signals in accordance with the timing signal, and wherein said selection means (9) is responsive to the timing signal for exchanging the operations of supplying the first output signal to the external circuit and the second output signal to said control signal generating means.

4. An apparatus having an automatic gain control circuit of claim 1 for measuring a transmissivity of an object (43), comprising:
   means (41, 42) for irradiating light emitted from a single source of light on the object before inputting said first and second input signals into said automatic gain control circuit;
   a first conversion means (1, 2, 44) for transmitting part of the light from the source through an optical fiber to a first light receiving element and for converting an output signal of the first light receiving element to the second signal; and
   a second conversion means (3, 4, 45) for transferring light transmitted through the object by way of an optical fiber to a second light receiving element and for converting an output signal of the second light receiving element to the first signal.

5. An apparatus having an automatic gain control circuit of claim 1 for measuring a reflectivity of an object, comprising:
   means (41, 42) for irradiating light emitted from a single source of light on the object before inputting said first and second input signals into said automatic gain control circuit;
   a first conversion means (1, 2, 44) for transmitting part of the light from the source through an optical fiber to a first light receiving element and for converting an output signal of the first light receiving element to the second signal; and
   a second conversion means (3a, 4a, 45a) for transferring light reflected by the object through an optical fiber to a second light receiving element and for converting an output signal of the second light receiving element to the first signal.

6. An apparatus having an automatic gain control circuit of claim 1 for measuring a reflectivity and transmissivity of an object, comprising:

means (41, 42) for irradiating light emitted from a single source of light on the object before inputting said first and second input signals into said automatic gain control circuit;

a first conversion means (1, 2, 44) for transmitting part of the light from the source through an optical fiber to a first light receiving element and for converting an output signal of the first light receiving element to the second signal;

a second conversion means for transferring light reflected by the object through an optical fiber to a second light receiving element and for converting an output signal of the second light receiving element to the first signal; and a third conversion means for transferring light transmitted through the object by way of an optical fiber to a third light receiving element and for converting an output signal of the third light receiving element to the first signal.

* * * * *